United States Patent
Pielka et al.

(10) Patent No.: US 12,104,620 B2
(45) Date of Patent: Oct. 1, 2024

(54) BEARING ASSEMBLY AND ROTARY FLUID PUMP

(71) Applicant: Berlin Heart GmbH, Berlin (DE)

(72) Inventors: Sascha Pielka, Berlin (DE); Bodo Schmidt, Teltow (DE)

(73) Assignee: Berlin Heart GmbH, Berlin (DE)

( * ) Notice: Subject to any disclaimer, the term of this patent is extended or adjusted under 35 U.S.C. 154(b) by 660 days.

(21) Appl. No.: 17/280,350

(22) PCT Filed: Sep. 26, 2019

(86) PCT No.: PCT/EP2019/076033
§ 371 (c)(1),
(2) Date: Mar. 26, 2021

(87) PCT Pub. No.: WO2020/069965
PCT Pub. Date: Apr. 9, 2020

(65) Prior Publication Data
US 2021/0346679 A1    Nov. 11, 2021

(30) Foreign Application Priority Data
Oct. 2, 2018  (EP) .................................. 18198373

(51) Int. Cl.
*F04D 7/00* (2006.01)
*A61M 60/122* (2021.01)
(Continued)

(52) U.S. Cl.
CPC ............. *F04D 7/00* (2013.01); *A61M 60/122* (2021.01); *A61M 60/216* (2021.01);
(Continued)

(58) Field of Classification Search
CPC .......... F04D 7/00; F04D 3/00; A61M 60/122; A61M 60/216; A61M 60/82;
(Continued)

(56) References Cited

U.S. PATENT DOCUMENTS 5,840,070 A    11/1998  Wampler
5,947,609 A     9/1999  Lee
(Continued)

FOREIGN PATENT DOCUMENTS

DE          198 22 587 A1    11/1999
DE    10 2008 037 677 A1     2/2010
(Continued)

OTHER PUBLICATIONS

Machine Translation of WO-2019054280-A1 (Year: 2019).*
Machine Translation of DE-102016216720-A1 (Year: 2018).*
International Search Report for Application No. PCT/EP2019/076033, dated Dec. 4, 2019, 6 pgs.

*Primary Examiner* — Brandon D Lee
(74) *Attorney, Agent, or Firm* — Crowell & Moring LLP

(57) ABSTRACT

A bearing assembly may be provided for mounting a rotor which can be rotated about a rotational axis. In particular, for a rotary fluid pump or rotary blood pump comprising: a main body, a bearing element which can be displaced relative to the main body in the direction of the rotational axis for receiving the rotor, and an adjusting device which is connected to the bearing element for displacing the bearing element in the direction of the rotational axis by a predefined distance, wherein the predefined distance is <=500 micrometres.

20 Claims, 9 Drawing Sheets

(51) Int. Cl.
  *A61M 60/216* (2021.01)
  *A61M 60/82* (2021.01)
  *A61M 60/825* (2021.01)
  *F04D 3/00* (2006.01)
  *F16C 25/04* (2006.01)

(52) U.S. Cl.
  CPC .......... *A61M 60/82* (2021.01); *A61M 60/825* (2021.01); *F04D 3/00* (2013.01); *F16C 25/04* (2013.01); *F16C 2202/36* (2013.01)

(58) Field of Classification Search
  CPC ... A61M 60/825; A61M 60/824; F16C 25/04; F16C 2202/22; F16C 2202/36; F16C 2240/46; F16C 2316/18; F16C 23/048; F16C 33/105; F16C 35/02; F16C 17/08
  See application file for complete search history.

(56) References Cited

U.S. PATENT DOCUMENTS

| | | | |
|---|---|---|---|
| 2012/0095281 A1* | 4/2012 | Reichenbach | A61M 60/183 600/16 |
| 2019/0298902 A1* | 10/2019 | Siess | A61M 60/232 |

FOREIGN PATENT DOCUMENTS

| | | | |
|---|---|---|---|
| DE | 10 2008 052 261 A1 | | 4/2010 |
| DE | 10 2016 207 698 A1 | | 11/2017 |
| DE | 102016216720 A1 | * | 3/2018 |
| GB | 2 169 361 A | | 7/1986 |
| JP | 63084417 U | | 1/1991 |
| WO | WO 2013/152850 A1 | | 10/2013 |
| WO | WO-2019054280 A1 | * | 3/2019 ........... B24B 41/047 |

* cited by examiner

BEARING ASSEMBLY AND ROTARY FLUID PUMP

CROSS-REFERENCE TO RELATED APPLICATIONS

This application is a 371 nationalization of international patent application PCT/EP2019/076033 filed Sep. 26, 2019, which claims priority under 35 USC § 119 to European patent application 18198373.5 filed Oct. 2, 2018. The entire contents of each of the above-identified applications are hereby incorporated by reference.

DETAILED DESCRIPTION

Figure 1:
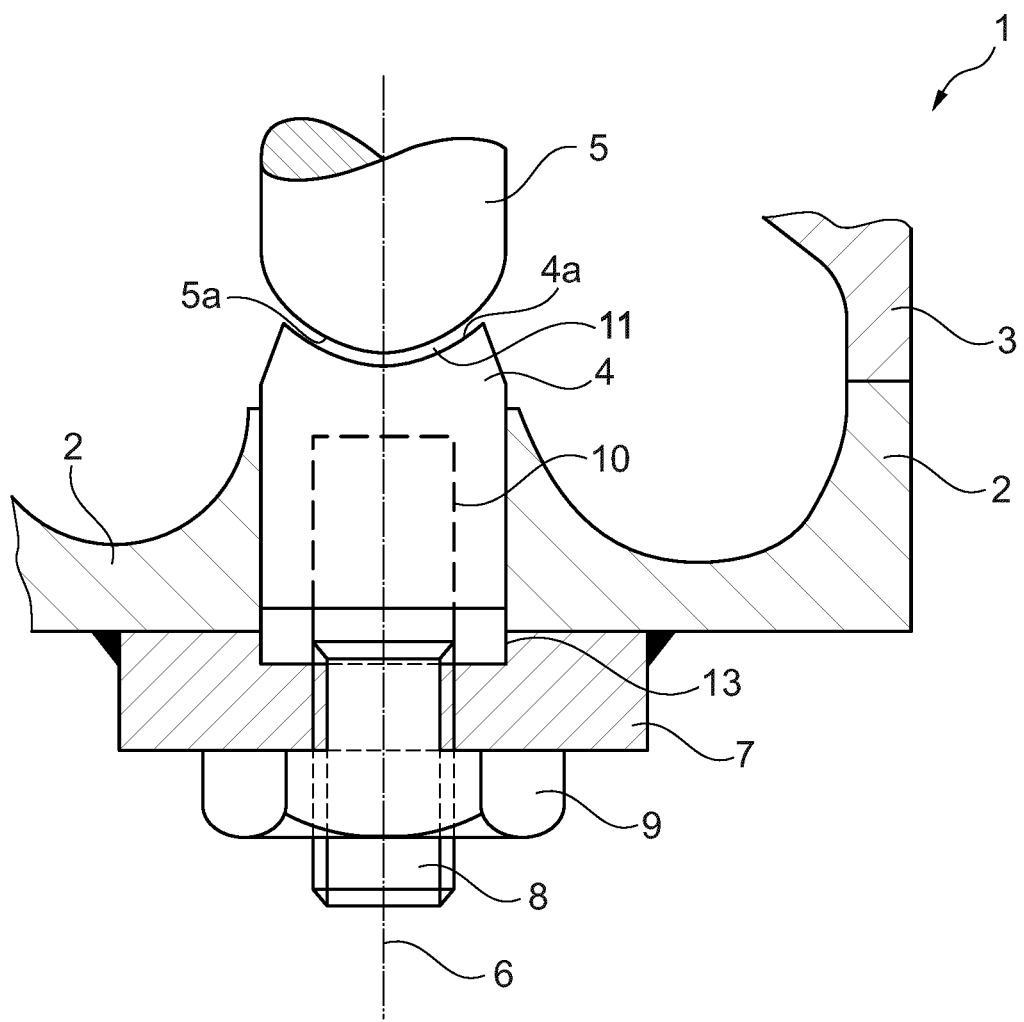
FIG. 1 shows a bearing assembly according to a first exemplary embodiment of the invention in an axial sectional view.

The present invention relates to a bearing assembly for mounting a rotor that can be rotated about a rotation axis, in particular for a rotary fluid pump. The invention further relates a rotary fluid pump for conveying a fluid, and in particular a rotary blood pump for conveying blood.

In the prior art, rotary fluid pumps are known, in which the rotor is axially and radially mounted in a purely mechanical, mechanical-magnetic or hydrodynamic manner. These bearings in general have a defined bearing gap between the rotor and the bearing element of the stator, which accommodates the rotor in the region of the rotation axis. The bearing gap has to be dimensioned in such a way that a certain liquid fraction of the blood pumped through the rotary blood pump finds its way between the two bearing components for lubricating the bearing. The lubrication has the advantage that the friction in the bearing is decreased, whereby excessive heating of protein present in the blood is prevented. In addition, no solid components present in the blood should enter the bearing gap since these increase hemolysis and promote thrombus growth. Setting a defined bearing gap is therefore necessary for the rotor to run smoothly and greatly influences the potential of the rotary blood pump to damage the blood.

In known mechanically mounted axial flow pumps, the bearing gap of the two ball cap bearings situated on the inlet side and the outlet side is set by a complex measurement process of the individual components, and subsequent adaptation of the parts by manual reworking (such as lapping, grinding, and the like). However, this is a very complex manual procedure that is only reproducible to a limited extent. Despite the extensive work that is involved for setting a defined bearing gap, these axial flow pumps show a high thrombogenicity risk.

It is therefore the object of the present invention to provide a bearing assembly that makes it possible to reproducibly set a dimensionally defined bearing gap in a rotary fluid pump. Another object of the invention is to provide a rotary fluid pump for conveying a fluid, comprising a bearing assembly according to the invention.

The bearing assembly according to the invention for mounting a rotor that can be rotated about a rotation axis, in particular for a rotary fluid pump, comprises a base body, a bearing element, which is displaceable relative to the base body in the direction of the rotation axis, for accommodating the rotor, and a adjusting device, which is connected to the bearing element, for displacing the bearing element in the direction of the rotation axis by a predetermined distance, wherein the predetermined distance is ≤500 μm.

After completion and assembly of the bearing components to form a bearing assembly and, for example, after installation in a rotary fluid pump, the bearing assembly according to the invention thus makes it possible to change and set the position of the bearing element in the micrometer range. In particular, the bearing assembly according to the invention makes it possible to set the bearing gap between the rotor and the bearing element in a dimensionally defined and reproducible manner.

The bearing assembly according to the invention can, for example, be used in a rotary blood pump for conveying blood, and in particular in an implantable rotary blood pump. In the rotary blood pump, the bearing assembly according to the invention makes it possible to decrease the potential of the rotary blood pump to damage the blood as a result of the ability to set the bearing gap between the bearing element and the rotor in a dimensionally defined manner.

In a particularly preferred variant embodiment of the bearing assembly according to the invention, the predetermined distance can be 250 μm, in particular 100 μm, in particular 50 μm, in particular 20 μm, preferably 15 μm, particularly preferably 10 μm, and in particular 5 μm. In these instances, a particularly fine displacement of the bearing element and a particularly fine setting of the bearing gap are possible.

The bearing assembly can be an integral part of a mechanical and/or hydrodynamic bearing, in particular of a ball cap bearing, a mechanical-magnetic bearing and/or a safety bearing.

The bearing element can include a bearing surface for receiving the rotor, wherein the adjusting device is arranged on a side of the bearing element facing away from the bearing surface. When the bearing assembly is used in a pump housing, the adjusting device is thus preferably essentially situated outside the actual pump housing, so as to be operable from outside, even after installation of the bearing assembly.

In another preferred exemplary embodiment of the invention, the adjusting device can comprise a screw element, which is connected to the bearing element in such a way that a rotation of the screw element by a predetermined angle causes a displacement of the bearing element by the predetermined distance.

In particular, a rotation of the screw element by 45° can cause a displacement of the bearing element by 25 μm. This enables a very fine and highly reproducible displacement of the bearing element, and thus a very fine and highly reproducible setting of the bearing gap between the rotor and the bearing element.

According to another possible exemplary embodiment, the adjusting device comprises a fine threaded spindle and a threaded washer, wherein the threaded washer is rigidly connected to the base element, and wherein the fine threaded spindle is rigidly connected to the bearing element in the direction of the rotation axis and screwed into the threaded washer so that a screwing motion of the fine threaded spindle in the threaded washer by a predetermined angle causes a displacement of the bearing element by the predetermined distance.

The adjusting device can furthermore comprise a lock nut. After a position of the bearing element has been set, the fine threaded spindle can be fixed by way of the lock nut. The lock nut can, for example, be screwable or screwed onto the fine threaded spindle on a side of the threaded washer facing away from the bearing element. The fixation by way of the lock nut enables a particularly stable fixation of the position of the bearing element, whereby the bearing assembly becomes stronger and tougher, for example to the action of an external force.

It is particularly advantageous when a spring element is arranged between the bearing element and the threaded washer, which prestresses the fine threaded spindle with respect to the threaded washer. In this way, a thread backlash between the threaded washer and the fine threaded spindle can be reduced.

According to another possible exemplary embodiment, the adjusting device comprises a segment plate including at least four segments arranged in a cross-shaped manner, wherein the segment plate, in two opposing segments, includes regions that are raised toward the base body and have a predetermined height, and the base body includes recessed regions located opposite the raised regions of the segment plate so that, in a first position of the segment plate, the raised and recessed regions can engage one another, and so that a rotation of the segment plate into a second position, in which the raised and recessed regions do not engage one another, causes a displacement of the bearing element by the predetermined distance, wherein the predetermined distance corresponds to the predetermined height of the raised regions. The raised regions can, in particular, have a height of ≥3 μm and/or ≤20 μm, preferably ≥5 μm and/or ≤15 μm. The raised regions, however, can also have other heights, for example <3 μm or >20 μm. The segment plate can be fixable in a desired position, in particular the second position, by means of a fixation device, for example a clamping device and/or a screw fixation device (for example a screw fixation device comprising a fine threaded spindle and a lock nut).

Using the segment plate, it is possible to set the position of the bearing element, and thus of the bearing gap, in a particularly precise, reproducible and stable manner.

According to another possible exemplary embodiment, the adjusting device comprises a fine threaded spindle, a segment plate including at least four segments arranged in a cross-shaped manner, and a lock nut, wherein the fine threaded spindle is rigidly connected to the bearing element in the direction of the rotation axis and, on a side facing away from the bearing element, is screwed into the segment plate and fixed in the segment plate by way of the lock nut, and wherein the segment plate, in two opposing segments, includes regions that are raised toward the base body and have a predetermined height, and the base body includes recessed regions located opposite the raised regions of the segment plate so that, in a first position of the segment plate, the raised and recessed regions can engage one another, and so that a rotation of the segment plate into a second position, in which the raised and recessed regions do not engage one another, causes a displacement of the bearing element by the predetermined distance, wherein the predetermined distance corresponds to the predetermined height of the raised regions. The raised regions can, in particular, have a height of ≥3 μm and/or ≤20 μm, preferably ≥5 μm and/or ≤15 μm.

According to another possible exemplary embodiment, the adjusting device comprises a segment plate including at least four segments arranged in a cross-shaped manner and a clamping device, wherein the bearing element is inserted into the segment plate in the direction of the rotation axis and is fixed by way of the clamping device, and wherein the segment plate, in two opposing segments, includes regions that are raised toward the base body and have a predetermined height, and the base body includes recessed regions located opposite the raised regions of the segment plate so that, in a first position of the segment plate, the raised and recessed regions can engage one another, and so that a rotation of the segment plate into a second position, in which the raised and recessed regions do not engage one another, causes a displacement of the bearing element by the predetermined distance, wherein the predetermined distance corresponds to the predetermined height of the raised regions. The raised regions can, in particular, have a height of ≥3 μm and/or ≤20 μm, preferably ≥5 μm and/or ≤15 μm.

In particular, the bearing element can be fixable in the direction of the rotation axis by way of a holding device, which engages on a segment of the segment plate and is attached to the base body.

The raised regions can be producible by way of a machining process, in particular by way of a grinding process, and/or by way of an additive process, in particular by way of a vapor deposition process, a printing process and/or a coating process.

According to another possible exemplary embodiment, the adjusting device comprises a tapered washer including two diametrically arranged tapered surfaces that are inclined in a circumferential direction of the tapered washer, wherein the bearing element is screwed into the tapered washer so that a rotation of the tapered washer by a predetermined angle causes a displacement of the bearing element by the predetermined distance.

According to another possible exemplary embodiment, the bearing element, on a side of the bearing element facing away from the rotor to be accommodated, includes a wedge-shaped section, and the adjusting device comprises a disk-shaped element having a funnel-shaped through-opening, wherein the bearing element is inserted with the wedge-shaped section into the funnel-shaped through-opening and rigidly connected to a termination element, and wherein furthermore the adjusting device comprises a spring element, which is arranged between the disk-shaped element and the termination element and prestresses the disk-shaped element with respect to the bearing element, and comprises a clamping screw arranged in the disk-shaped element, by way of which a diameter of the wedge-shaped through-opening can be changed by a predetermined magnitude, so that a change of the diameter by a predetermined diameter difference causes a displacement of the bearing element by the predetermined distance.

According to another possible exemplary embodiment, the adjusting device comprises a lever, which is connected to the bearing element so that a change in the inclination of the lever relative to the base body by a predetermined angular difference causes a displacement of the bearing element by the predetermined distance.

According to another possible exemplary embodiment, the adjusting device comprises an element having a predetermined coefficient of thermal expansion, wherein the element is connected to the bearing element in such a way that a change of a temperature of the element by a predetermined temperature amount causes a displacement of the bearing element by the predetermined distance.

According to another possible exemplary embodiment, the adjusting device comprises a piezo element, which is connected to the bearing element in such a way that an application of a predetermined voltage to the piezo element causes a displacement of the bearing element by the predetermined distance.

In particular, the piezo element can be detachably connected to the bearing element.

The present invention also encompasses a rotary fluid pump for conveying a fluid, and in particular a rotary blood pump or an implantable rotary blood pump for conveying blood, which comprises an above-described bearing assembly.

In particular, the base element of the bearing assembly can be an integral part of a housing bottom of a pump housing of the rotary fluid pump, wherein the adjusting device is in particular situated outside the pump housing so as to be operable from outside, even after the bearing assembly has been installed in the pump housing.

Several exemplary embodiments of a bearing assembly according to the invention are described hereafter in greater detail based on figures. Different elements that are essential to the invention, or elements providing advantageous refinements, are described in each case within the scope of a specific example, wherein it is also possible to use individual of these elements per se to refine the invention, including detached from the context of the example and further features of the example. Moreover, identical or similar reference numerals are used for identical or similar elements in the figures, and the explanation thereof is therefore partially omitted.

FIG. 1 shows a bearing assembly 1 and the installation thereof in a rotary fluid pump, according to a first exemplary embodiment of the invention in an axial sectional view. The bearing assembly 1 comprises a base element 2 which is designed as a housing bottom 2 of the rotary fluid pump. The bearing assembly 1 is arranged in the region of a fluid outlet of the rotary fluid pump. Another housing part 3 adjoins the housing bottom 2 of the rotary fluid pump in the direction of a fluid inlet arranged upstream. The housing bottom 2 and the housing part 3 form parts of the pump housing, which is not shown completely here. A first bearing element 4 of the bearing assembly 1 extends approximately centrally through the housing bottom 2, perpendicular to the main extension plane of the housing bottom 2, and passes through the housing bottom 2. The first bearing element 4 is arranged in the housing bottom 2 so as to be displaceable in a perpendicular direction to the main extension plane of the housing bottom 2. A second bearing element 5, which is fixedly connected to a rotor (not shown here) of the rotary fluid pump, is mounted on the bearing element 4. The first bearing element 4 includes a dome-shaped bearing surface 4a in which a spherical bearing surface 5a of the second bearing element 5 engages. The bearing of the rotary fluid pump illustrated here is a ball cap bearing. This makes it possible for the second bearing element 5 to rotate in the first bearing element 4, about a rotation axis 6 that extends substantially perpendicular to the main extension plane of the housing bottom 2 and parallel to the passage direction of the bearing element 4 through the housing bottom 2. The position of the second bearing element 5 along the rotation axis 6, that is, in the axial direction, is essentially established by a second pump bearing, which is arranged on the inlet side and not illustrated here. For setting an axial position of the first bearing element 4, and thus a bearing gap 11 between the first bearing element 4 and the second bearing element 5, the bearing assembly 1 comprises a adjusting device 7, 8, 9, which is arranged on a side of the first bearing element 4 located opposite the bearing surface 4a of the first bearing element 4, outside the pump housing. The adjusting device 7, 8, 9 comprises a threaded washer 7, which is rigidly connected to the housing bottom 2 in a form-fit manner, and a fine threaded spindle 8 rigidly connected to the first bearing element 4. The fine threaded spindle 8 is coaxially inserted into a cylindrical opening 10 of the first bearing element 4 and glued or welded to the first bearing element 4 inside the first bearing element 4. The threaded washer 7 and the fine threaded spindle 8 include threads that are matched to one another, so that the fine threaded spindle 8 can be screwed into and out of the threaded washer 7. In the process, thread axes of the fine threaded spindle 8 and of the threaded washer 7 run coaxial to the rotation axis 6. By screwing the threaded spindle 8 into the threaded washer 7 or out of the threaded washer 7, the first bearing element 4 can be screwed further through the housing bottom 2 in the direction of the fluid inlet into the pump housing, so that the bearing gap 11 is reduced, or it can be screwed out of the pump housing so that the bearing gap 11 is increased. On a side facing the first bearing element 4, the threaded washer 7 includes a recess 13, having a diameter that is adapted to a diameter of the bearing element 4, so that the bearing element 4, when it has been sufficiently screwed out of the pump housing, is able to engage in the recess 13 in a form-fit manner. A rotation of the fine threaded spindle 8 by 45° results, for example, in an axial difference in distance of the first bearing element 4 of 25 µm. In this way, it is possible to very finely and reproducibly set the axial position of the first bearing element 4. So as to retain the axial position of the first bearing element 4, a lock nut 9 is screwed onto the fine threaded spindle 8 on a side of the threaded washer 7 which faces away from the first bearing element 4.

Figure 2:
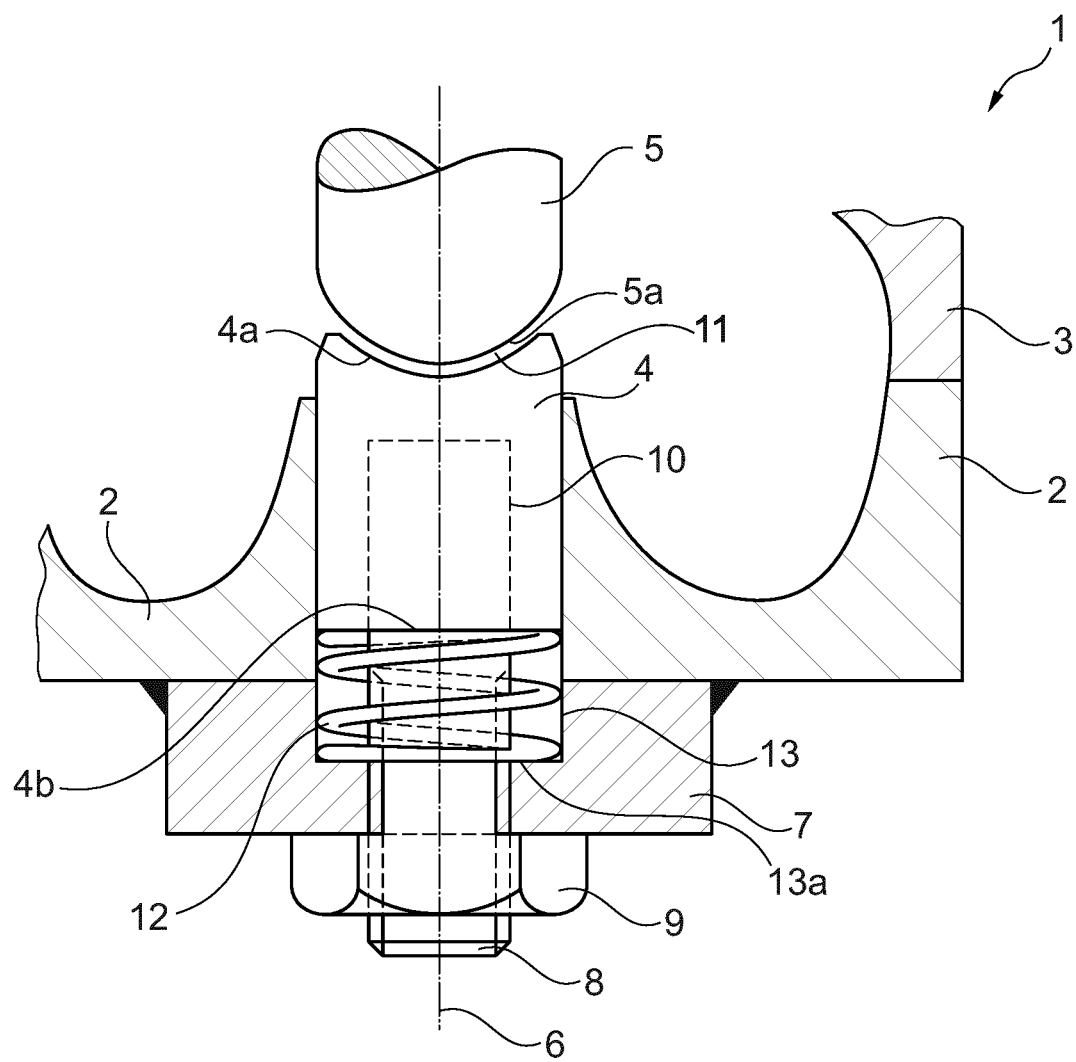
FIG. 2 shows a bearing assembly according to a second exemplary embodiment of the invention in an axial sectional view.

FIG. 2 shows a bearing assembly according to a second exemplary embodiment of the invention and the installation thereof into a rotary fluid pump in an axial sectional view. The bearing assembly 1 according to the second exemplary embodiment and the installation thereof into a rotary fluid pump are similar to the first exemplary embodiment. In contrast to the first exemplary embodiment, the recess 13 of the threaded washer 7 is designed to be extended in the axial direction. Furthermore, a coil spring 12, which prestresses the fine threaded spindle 8 and the first bearing element 4 with respect to the threaded washer 7, is arranged between a surface 4b of the bearing element 4 located opposite the bearing surface 4a and a bottom surface 13a of the recess 13. In this way, a thread backlash between the threaded washer 7 and the fine threaded spindle 8 can be reduced and, as a result, the axial position of the first bearing element 4 can be set even more reproducibly.

Figure 3:
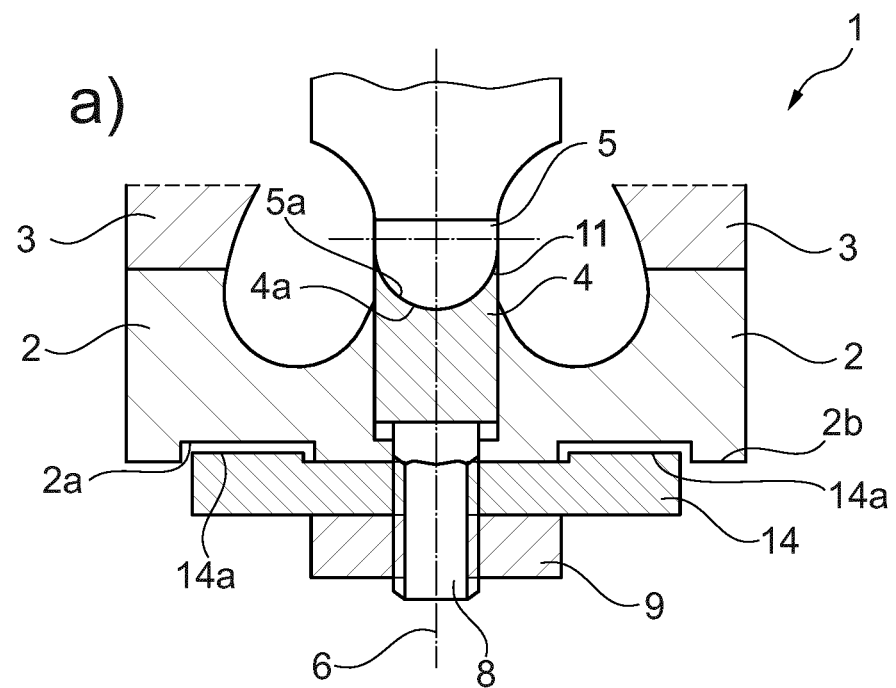
FIG. 3 shows a bearing assembly according to a third exemplary embodiment of the invention in an axial sectional view.
Figure 3:
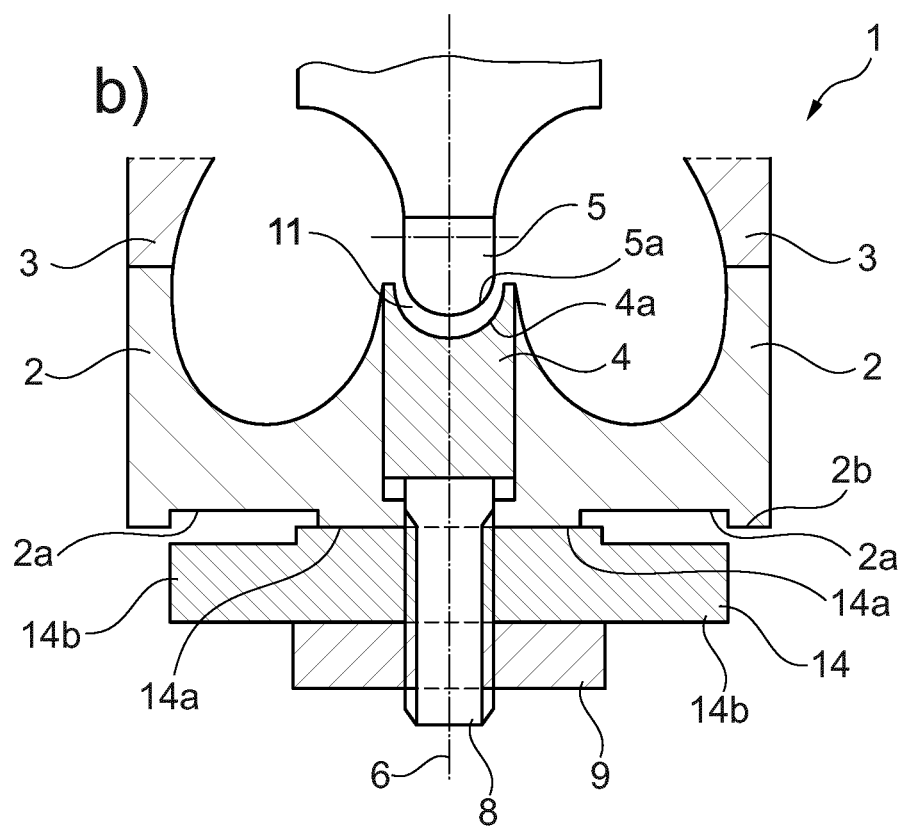

FIG. 3 shows a bearing assembly according to a third exemplary embodiment of the invention and the installation thereof into a rotary fluid pump in an axial sectional view. The bearing assembly 1 of the third exemplary embodiment is composed in a manner similar to the preceding exemplary embodiments. The third exemplary embodiment differs only in the specific design of the adjusting device. Here, the adjusting device 14, 8, 9, 2a essentially comprises a fine threaded spindle 8 rigidly connected to the first bearing element 4, as in FIGS. 1 and 2, a segment plate 14 comprising at least four segments 14a, 14b arranged in a cross-shaped manner, instead of the threaded washer 7, and a lock nut 9. The segment plate 14 is arranged in a form-fit manner at the housing bottom 2, on a side of the housing bottom 2 that faces away from the bearing surface 4a. The fine threaded spindle 8 is screwed into the segment plate 14, similarly to being screwed into the threaded washer 7 of FIGS. 1 and 2, and is thus rigidly connected to the segment plate 14 in the axial direction. Two opposing segments 14a of the four segments 14a, 14b include regions that are raised toward the housing bottom 2 and have a predetermined height. On the side facing away from the bearing surface 4a, the housing bottom 2 includes recessed regions 2a, corresponding to the raised regions of the segments 14a, so that the raised regions are able to engage in the recessed regions 2a (see FIG. 3a). In FIG. 3a), the further segments 14b preferably extend perpendicular to the drawing plane, that is, also perpendicular to the segments 14a. In the position of the segment plate 14 shown in FIG. 3a), in which the raised regions of the segments 14a engage completely in the recessed regions 2a, the housing bottom 2 and the segments 14b rest on top of one another in a form-fit manner. In this position of the adjusting device, the bearing surfaces 4a and 5a of the bearing elements 4 and 5 also rest directly on one another. The bearing gap is thus zero. In FIG. 3b), in contrast, the segments 14b without raised regions are located in the drawing plane, that is, opposite the recessed regions 2a. The segments 14a are located essentially perpendicular to the segments 14b, that is, extend perpendicular to the drawing plane. The raised regions of the segments 14a are not located opposite recessed regions 2a of the housing bottom 2 and cannot engage in these, but rest against the housing bottom surface 2b. In this way, the entire segment plate 14, and thus also the bearing element 4 that is rigidly connected to the segment plate 14 by way of the fine threaded spindle 8, is located further away from the second bearing element 5, resulting in the bearing gap 11. Compared to FIG. 3a), the axial position of the first bearing element 4 is thus shifted, directed away from the second bearing element 5, by the height of the raised regions.

So as to set the axial position of the bearing element 4, and thus the bearing gap 11, in a defined manner, proceeding from FIG. 3a), the bearing element 4 is pulled slightly out of the pump housing, and thus directed away from the second bearing element 5, by way of the fine threaded spindle 8. Thereafter, the fine threaded spindle 8 is rotated by 90°, so that the raised regions of the segments 14a rest against the housing bottom surface 2b. This position of the fine threaded spindle 8 within the segment plate 14 is then retained by way of the lock nut 9. So as to fix the segment plate 14, and thus the entire adjusting device and the first bearing element 4, relative in the housing bottom 2, clamping screws (not shown here) can be screwed into the housing bottom 2, on an outer side of the housing bottom 2 facing away from the rotation axis 6, on the housing bottom surface 2b, which clamp an outer side of the segments 14a) and/or 14b) between themselves and the housing bottom surface 2b. The height of the raised regions is preferably 10 µm, particularly preferably 8 µm, so that a rotation of the segment plate by 90° results in a difference in distance of the first bearing element 4 of preferably 10 µm, and accordingly particularly preferably 8 µm.

Figure 4:
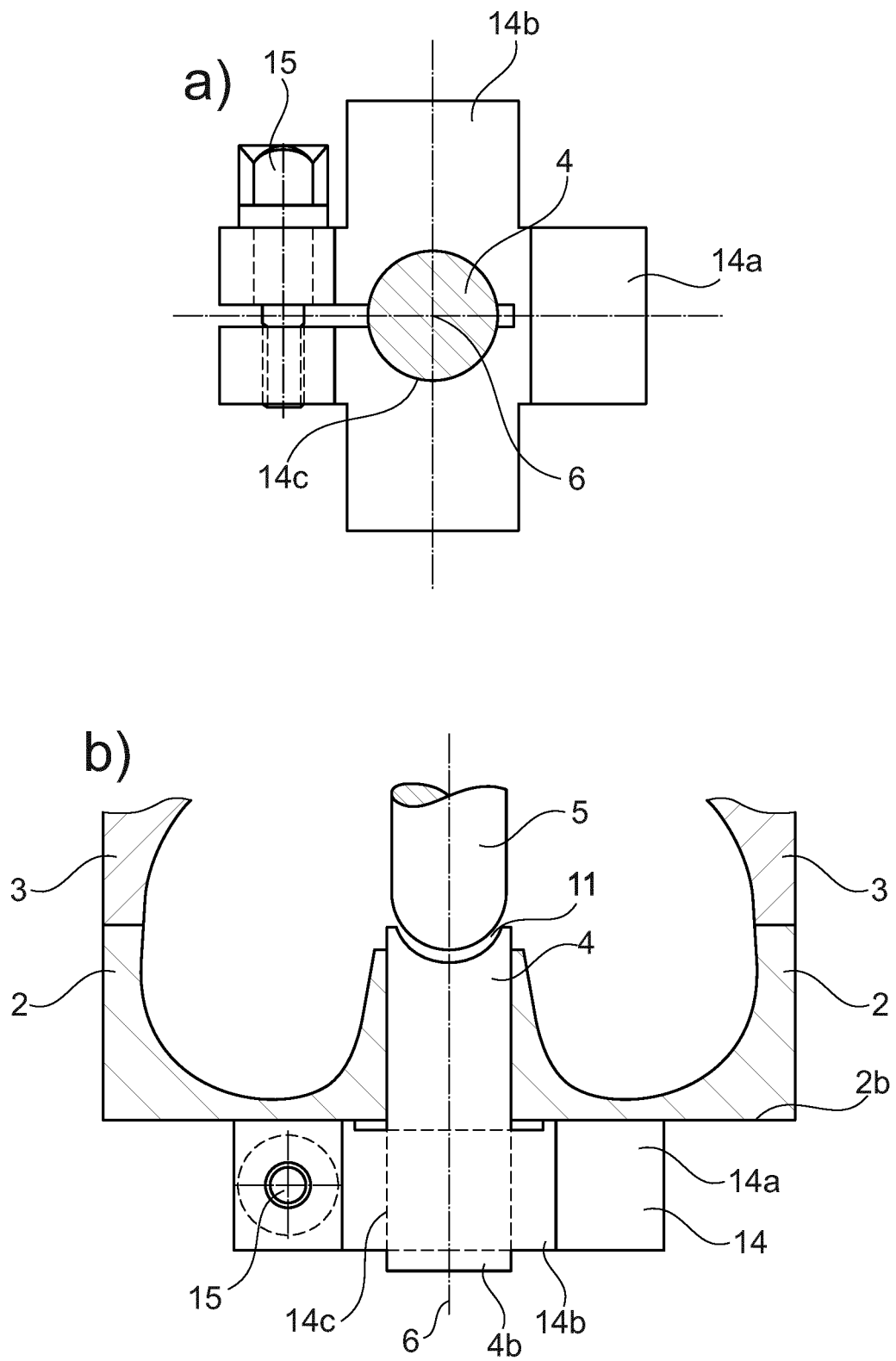
FIG. 4 shows a bearing assembly according to a fourth exemplary embodiment of the invention in an axial sectional view.

FIG. 4 shows a bearing assembly 1 according to a fourth exemplary embodiment of the invention and the installation thereof into a rotary fluid pump in an axial sectional view. The exemplary embodiment of FIG. 4 essentially differs from the exemplary embodiments one to three in the configuration of the adjusting device. In FIG. 4, the first bearing element 4 comprises an axially extended shaft 4b that is directed away from the second bearing element 5. This shaft 4b extends through a segment plate 14 designed similarly to that of FIG. 3. The segment plate 14 rests against the housing bottom surface 2b in a form-fit manner, and likewise comprises four segments 14a, 14b arranged in a cross-shaped manner, wherein two opposing segments 14a, as in FIG. 3, include raised regions. FIG. 4a) shows a top view onto the segment plate 14. So as to fix the segment plate 14 to the shaft 4b, the segment plate 14, in one of the segments 14a, comprises a clamping screw 15 by way of which a diameter of a through-opening 14c of the segment plate 14 through which the shaft 4b passes can be set.

So as to set a defined axial position of the first bearing element 4, and thus essentially a defined bearing gap 11, the segment plate 14 is initially pushed against the housing bottom surface 2a in such a way that the raised regions of the segments 14a engage in recessed regions of the housing bottom surface 2b (not shown here). Thereafter, the relative position between the shaft 4b and the segment plate 14 is fixed by tightening the clamping screw 15. The segment plate is then rotated by 90°, so that the raised regions of the segments 14a no longer engage in the recessed regions of the housing bottom surface 2b, but rest directly against the housing bottom surface 2b. In this way, the first bearing element 4 is located away from the second bearing element 5 by the height of the raised regions (preferably including 8 to 10 µm) in the direction of the housing bottom 2, resulting in a bearing gap 11 of approximately the height of the raised regions. This position including the bearing gap 11 is illustrated in FIG. 4b).

So as to attach the entire adjusting device and the first bearing element at the housing bottom 2, it is possible, as described in the third exemplary embodiment, for clamping screws to be screwed into the housing bottom 2 on the housing bottom surface 2b, which clamp the outer side of the segment plate to the housing bottom 2.

Figure 5:
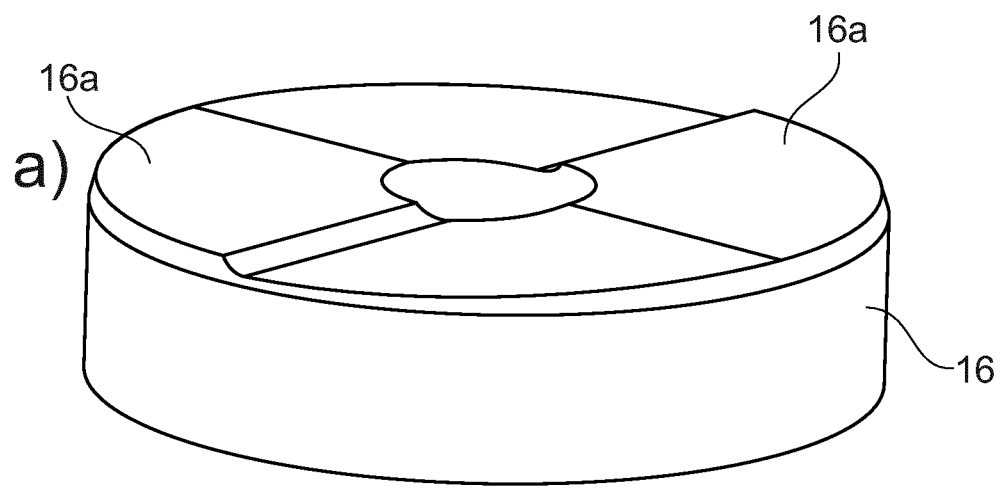
FIG. 5 shows a tapered washer as a component of a bearing assembly according to a fifth exemplary embodiment of the invention in perspective views.
Figure 5:
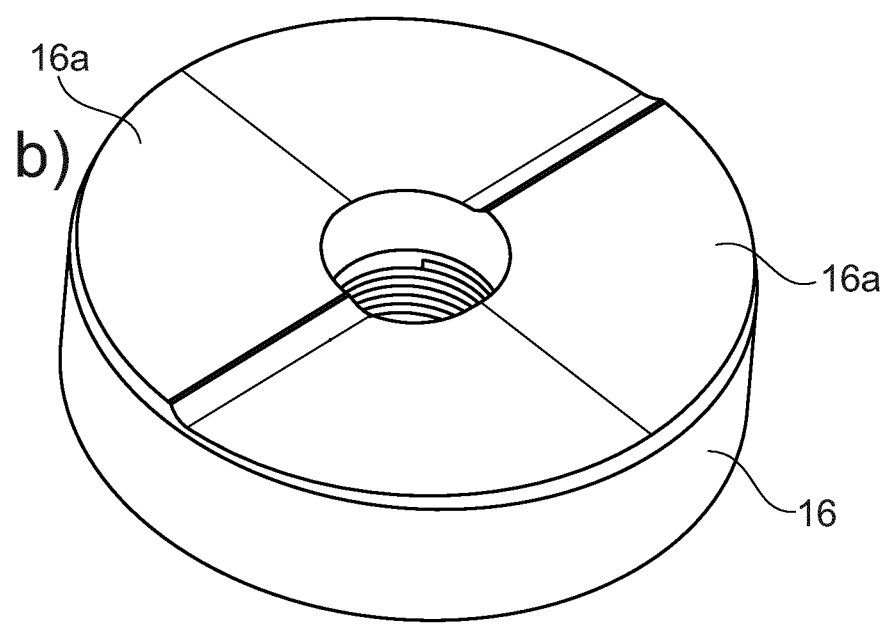

FIG. 5 shows a tapered washer 16 as a component of a bearing assembly 1 according to a fifth exemplary embodiment of the invention in perspective views a) and b). The tapered washer 16 is designed as a circular disk and, on a circular surface, includes diametrically arranged tapered surfaces 16a that ascend across approximately a circular segment of 45° in the axial direction and protrude from the circular surface. The tapered washer 16 can be used instead of the segment plate 14 in the third exemplary embodiment of FIG. 3. The elevated wedge surfaces 16a replace the raised regions of the segments 14a. The recessed regions in the housing bottom surface 2b are then likewise designed as accordingly recessed tapered surfaces, so that the tapered surfaces 16a can initially engage in the recessed wedge surfaces of the housing bottom surface 2b. In this position, the bearing gap 11 is then zero. A rotation of the tapered washer by 90° causes the raised tapered surfaces 16a to rotate completely out of the recessed tapered surfaces of the housing bottom surface 2b and to rest against the housing bottom surface 2b. This results in a bearing gap 11 which corresponds to a maximum height of the tapered surfaces.

Figure 6:
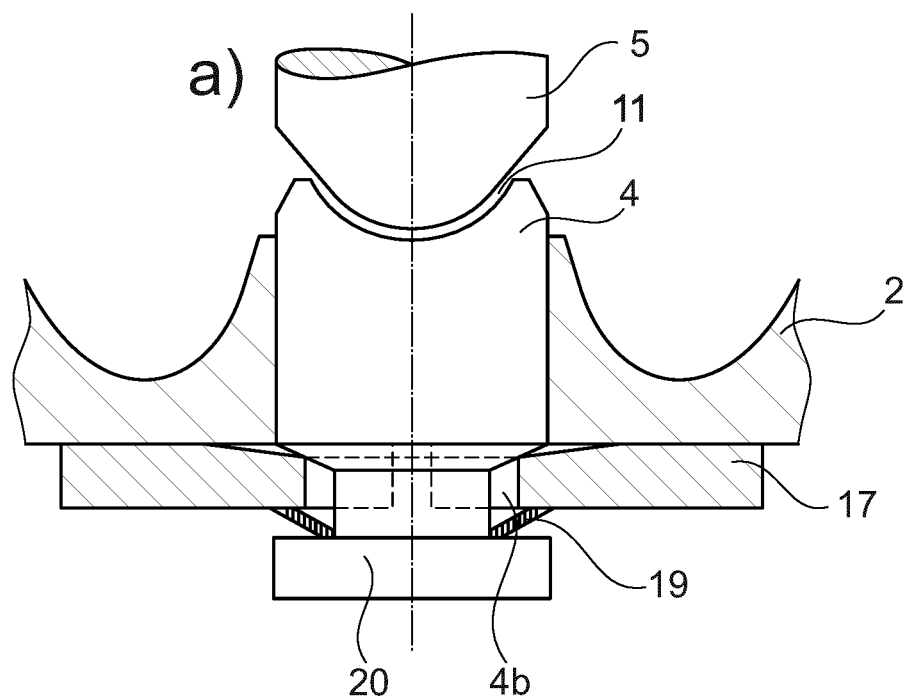
FIG. 6 shows a bearing assembly according to a sixth exemplary embodiment of the invention in an axial sectional view.
Figure 6:
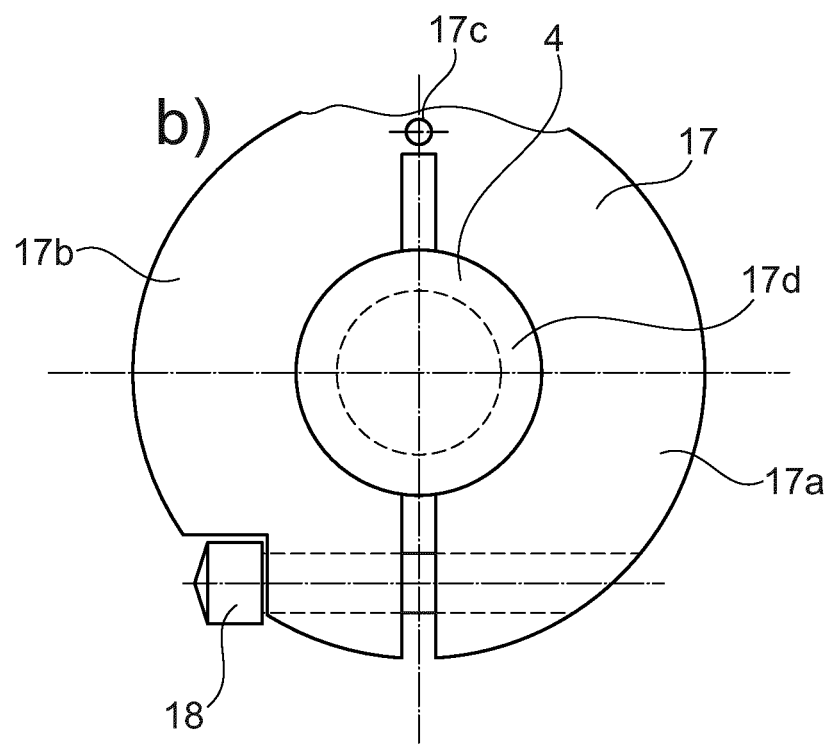

FIG. 6 shows a bearing assembly according to a sixth exemplary embodiment of the invention and the installation thereof into a rotary fluid pump in an axial sectional view. In the sixth exemplary embodiment, a two-piece tapered washer 17 is arranged at the housing bottom surface 2b, which comprises two semi-disks 17a and 17b connected to one another by a joint 17c (see FIG. 6 b)). A clamping screw 18, by way of which essentially a distance between the semi-disks 17a and 17b can be set, is arranged on a side of the tapered washer 17 located opposite the joint 17c. At the center, coaxial with the rotation axis 6, the tapered washer includes a through-opening 17d, through which the shaft 4b of the first bearing element 4 extends. A diameter of the through-opening 17d can likewise be varied by way of the clamping screw 18. On a side of the tapered washer 17 facing away from the first bearing element 4, the shaft is rigidly connected to a termination element 20, which prevents the tapered washer 17 from sliding off the shaft 4b. Furthermore, a spring 19 is arranged between the tapered washer 17 and the termination element 20, which prestresses the termination element 20 with respect to the tapered washer 17 and thus pulls the bearing element 4 toward the tapered washer 17. The through-opening is funnel-shaped in the axial direction. Furthermore, the shaft 4b has a wedge-shaped design in the region of the through-opening 17d, wherein the wedge of the shaft 4b preferably has a flatter angle of inclination than the funnel-shaped through-opening 17d. Due to the compressive force of the spring 19, the wedge-shaped shaft pushes on the funnel-shaped through-opening 17d. Screwing in the clamping screw 18 decreases the diameter of the through-opening 17d so that the funnel-shaped through-opening 17d pushes on the wedge-shaped shaft 4b. As a result, the wedge-shaped shaft, and thus the bearing element 4, is pushed to the bearing element 5. The bearing gap 11 decreases. Loosening the clamping screw 18 increases the diameter of the through-opening 17d, whereby the wedge-shaped surfaces of the shaft 4b and the through-opening push less on one another, and the spring 20 pulls the shaft 4b through the through-opening 17d. As a result, the bearing gap 11 increases.

Figure 7:
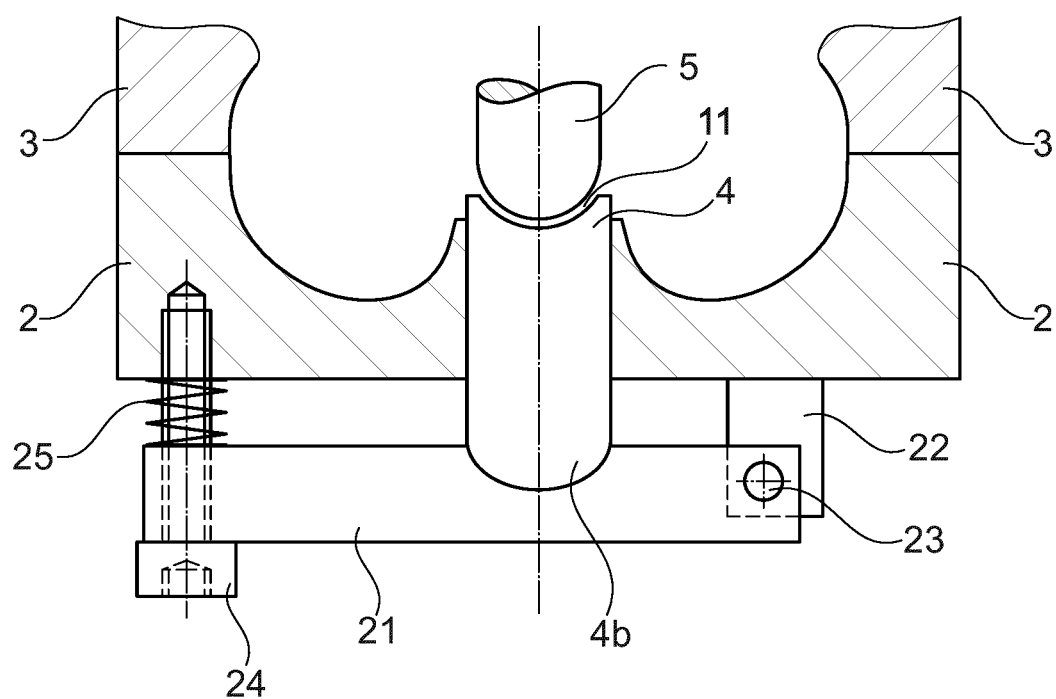
FIG. 7 shows a bearing assembly according to a seventh exemplary embodiment of the invention in an axial sectional view.

FIG. 7 shows a bearing assembly according to a seventh exemplary embodiment of the invention and the installation thereof into a rotary fluid pump in an axial sectional view. In the seventh exemplary embodiment, the shaft 4b is pushed by way of a lever 21 into the pump housing, and thus to the second bearing element 5, whereby the bearing gap 11 is decreased, or is pulled away from the second bearing element 5, out of the pump housing, so that the bearing gap 11 increases. The lever 21 is connected to the housing bottom 2 by way of a holding element 22 and a joint 23. At a distance of approximately one third the length of the lever 21 to the joint 23, the lever 21 is connected to the shaft 4b. On the side located opposite the joint 23, the lever 21 comprises an adjusting screw 24, which can be screwed into and out of the housing bottom 2 and by way of which a distance between the end of the lever 21 located opposite the joint 23 and the housing bottom surface 2b can be varied. The adjusting screw 24 furthermore extends through a spiral spring 25 arranged between the lever 21 and the housing bottom surface 2b, which prestresses the lever 21 with respect to the housing bottom 2, and thus decreases the thread backlash of the adjusting screw 24. By screwing the adjusting screw 24 in or out, an axial position of the first bearing element 4 in the direction of the second bearing element 5, or counter to the direction of the second bearing element 5, can be changed, and thus the bearing gap 11 can be decreased or increased.

Figure 8:
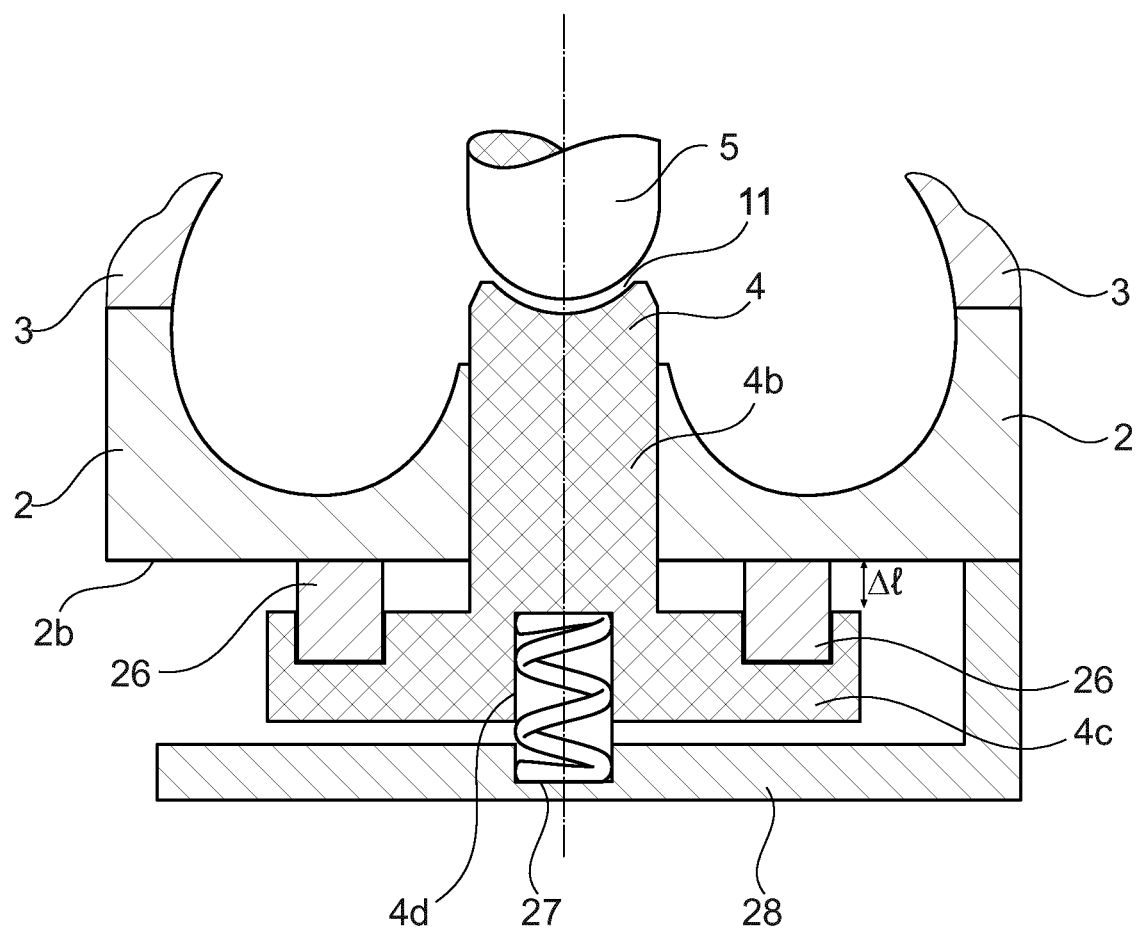
FIG. 8 shows a bearing assembly according to an eighth exemplary embodiment of the invention in an axial sectional view.

FIG. 8 shows a bearing assembly according to an eighth exemplary embodiment of the invention and the installation thereof into a rotary fluid pump in an axial sectional view. In the eighth exemplary embodiment, the axial position of the first bearing element 4 or of the bearing gap 11 is set by way of elements 26 having a predetermined coefficient of thermal expansion. For this purpose, the shaft 4b is rigidly connected to a plate 4c, which runs parallel to the housing bottom surface 2b and at a distance from the housing bottom 2. The elements 26 having a predetermined coefficient of thermal expansion are arranged between the housing bottom 2 and the plate 4c. A support plate 28 is arranged on a side of the plate 4c facing away from the housing bottom surface 2b, which runs parallel to and at a distance from the plate 4c and is rigidly connected to the housing bottom 2. Furthermore, a spiral spring 27 is arranged between the plate 4c and the support plate 28, which exerts a mutual compressive force on the plate 4c and the support plate 28, and thereby prestresses the plate 4c with respect to the support plate 28. For guidance purposes, the spiral spring 27 is inserted into opposite cylindrical grooves 4d and 28a in the plate 4c and in the support plate 28 in the region of the rotation axis 6.

The axial position of the first bearing element is set by the elements 26 experiencing a predetermined temperature difference, and thereupon expanding or contracting to a defined degree. In the case of a decrease of the bearing gap 11, the temperature of the elements 26 is decreased, whereupon these exert reduced pressure on the plate 4c. When the spring 27 overcomes the compressive force of the elements 27, the first bearing element 4 is pushed to the second bearing element 5. In the case of a decrease of the bearing gap 11, the temperature of the elements 26 is increased, whereby the elements expand and the compressive force thereof on the plate 4c is increased. When the compressive force of the elements 26 overcomes the compressive force of the spring 27, the first bearing element 4 is pulled away from the second bearing element 5.

Preferably, metals experiencing large thermal expansion are used for the elements 26. For example, a 20-fold thermal expansion is required to set the bearing gap 11.

Figure 9:
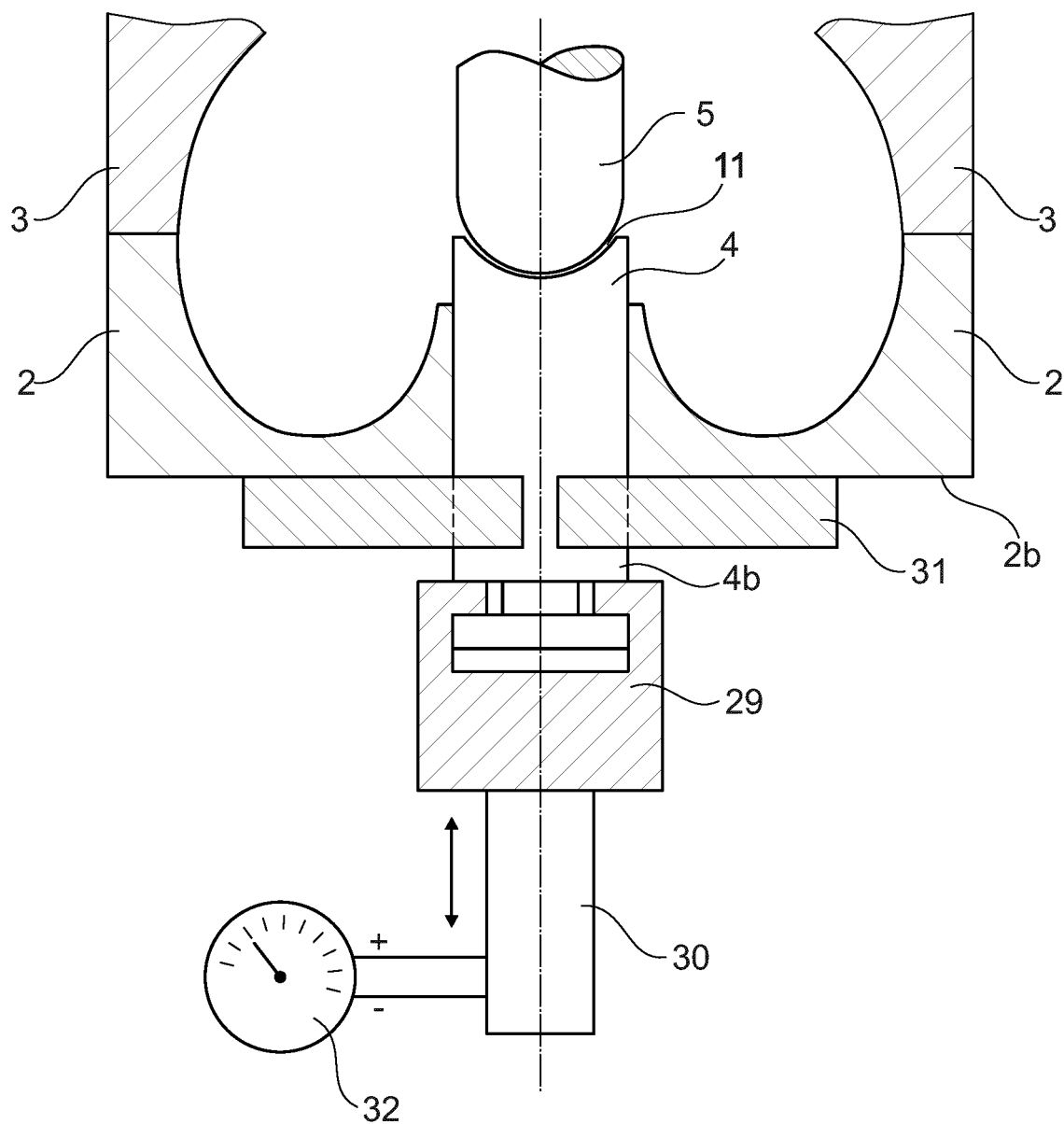
FIG. 9 shows a bearing assembly according to a ninth exemplary embodiment of the invention in an axial sectional view.

FIG. 9 shows a bearing assembly according to a ninth exemplary embodiment of the invention and the installation thereof into a rotary fluid pump in an axial sectional view. In this ninth exemplary embodiment, the shaft 4b is rigidly connected to a piezo actuator 30 by way of a coupling 29. Using the regulating device 32 connected to the piezo actuator 30, a defined voltage can be applied to the piezo actuator 30. The piezo actuator expands or contracts as a result of the change in voltage, and can thus vary the axial position of the first bearing element 4 by way of the shaft 4b. When the axial position of the first bearing element 4 or the bearing gap 11 has been set, the axial position of the bearing element 4 can be fixed by way of a clamping element 31 resting against the housing bottom surface 2b.

For setting the axial position or the bearing gap, the entire rotary fluid pump is inserted into a holding device. The coupling 29 is preferably connected without backlash to the shaft 4b and can be detached from the shaft 4b again after the axial position of the first bearing element 4 or the bearing gap has been set. In particular, the ninth exemplary embodiment described here allows the axial position of the first bearing element 4 to be set particularly precisely and reproducibly.

To clarify the use of and to hereby provide notice to the public, the phrases "at least one of <A>, <B>, ... and <N>" or "at least one of <A>, <B>, ... <N>, or combinations thereof" or "<A>, <B>, ... and/or <N>" are defined by the Applicant in the broadest sense, superseding any other implied definitions hereinbefore or hereinafter unless expressly asserted by the Applicant to the contrary, to mean one or more elements selected from the group comprising A, B, ... and N. In other words, the phrases mean any combination of one or more of the elements A, B, ... or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention furthermore relates to the following aspects:

1. A bearing assembly for mounting a rotor that can be rotated about a rotation axis, in particular for a rotary fluid pump or a rotary blood pump, comprising:
   a base body;
   a bearing element, which is displaceable relative to the base body in the direction of the rotation axis, for accommodating the rotor; and
   a adjusting device, which is connected to the bearing element, for displacing the bearing element in the direction of the rotation axis by a predetermined distance, the predetermined distance being ≤500 μm.

2. The bearing assembly according to the preceding aspect, characterized in that the predetermined distance is ≤100 μm, in particular ≤50 μm, preferably ≤20 μm, particularly preferably ≤10 μm, and in particular ≤5 μm.

3. The bearing assembly according to any one of the preceding aspects, characterized in that the adjusting device can comprise a screw element, which is connected to the bearing element in such a way that a rotation of the screw element by a predetermined angle causes a displacement of the bearing element by the predetermined distance.

4. The bearing assembly according to the preceding aspects, characterized in that a rotation of the screw element by 45° causes a displacement of the bearing element by 25 μm.

5. The bearing assembly according to any one of the preceding aspects, characterized in that the adjusting device comprises a fine threaded spindle and a threaded washer, the threaded washer being rigidly connected to the base element, and the fine threaded spindle being rigidly connected to the bearing element in the direction of the rotation axis and screwed into the threaded washer so that a screwing motion of the fine threaded spindle in the threaded washer by a predetermined angle causes a displacement of the bearing element by the predetermined distance.

6. The bearing assembly according to the preceding aspect, characterized in that a spring element is arranged between the bearing element and the threaded washer, which prestresses the fine threaded spindle with respect to the threaded washer.

7. The bearing assembly according to any one of aspects 1 to 4, characterized in that the adjusting device comprises fine threaded spindle, a segment plate including at least four segments arranged in a cross-shaped manner, and a lock nut, the fine threaded spindle being rigidly connected to the bearing element in the direction of the rotation axis and, on a side facing away from the bearing element, being screwed into the segment plate and fixed in the segment plate by way of the lock nut, and the segment plate, in two opposing segments, including regions that are raised toward the base body and have a predetermined height, and the base body including recessed regions located opposite the raised regions of the segment plate so that, in a first position of the segment plate, the raised and recessed regions can engage one another, and so that a rotation of the segment plate into a second position, in which the raised and recessed regions do not engage one another, causes a displacement of the bearing element by the predetermined distance, the predetermined distance corresponding to the predetermined height of the raised regions.

8. The bearing assembly according to any one of aspects 1 to 4, characterized in that the adjusting device comprises a segment plate including at least four segments arranged in a cross-shaped manner and a clamping device, the bearing element being inserted into the segment plate in the direction of the rotation axis and being fixed by way of the clamping device, and the segment plate, in two opposing segments, including regions that are raised toward the base body and have a predetermined height, and the base body including recessed regions located opposite the raised regions of the segment plate so that, in a first position of the segment plate, the raised and recessed regions can engage one another, and so that a rotation of the segment plate into a second position, in which the raised and recessed regions do not engage one another, causes a displacement of the bearing element by the predetermined distance, the predetermined distance corresponding to the predetermined height of the raised regions.

9. The bearing assembly according to any one of two preceding aspects, characterized in that the raised regions can be producible by way of a machining process, in particular by way of a grinding process, and/or by way of an additive process, in particular by way of a vapor deposition process, a printing process and/or a coating process.

10. The bearing assembly according to any one of aspects 1 to 4, characterized in that the adjusting device comprises a tapered washer including two tapered surfaces that are arranged diametrically offset and inclined in a circumferential direction of the tapered washer, the bearing element being screwed into the tapered washer so that a rotation of the tapered washer by a predetermined angle causes a displacement of the bearing element by the predetermined distance.

11. The bearing assembly according to any one of aspects 1 to 4, characterized in that the bearing element, on a side of the bearing element facing away from the rotor to be accommodated, includes a wedge-shaped section, and the adjusting device comprises a disk-shaped element having a funnel-shaped through-opening, the bearing element being inserted with the wedge-shaped section into the funnel-shaped through-opening and rigidly connected to a termination element, and furthermore the adjusting device comprising a spring element, which is arranged between the disk-shaped element and the termination element and prestresses the disk-shaped element with respect to the bearing element, and comprising a clamping screw arranged in the disk-shaped element, by way of which a diameter of the wedge-shaped through-opening can be changed by a predetermined magnitude, so that a change of the diameter by a predetermined diameter difference causes a displacement of the bearing element by the predetermined distance.

12. The bearing assembly according to any one of aspects 1 to 4, characterized in that the adjusting device comprises a lever, which is connected to the bearing element so that a change in the inclination of the lever relative to the base body by a predetermined angular difference causes a displacement of the bearing element by the predetermined distance.

13. The bearing assembly according to any one of aspects 1 to 4, characterized in that the adjusting device comprises an element having a predetermined coefficient of thermal expansion, the element being connected to the bearing element in such a way that a change of a temperature of the element by a predetermined temperature amount causes a displacement of the bearing element by the predetermined distance.

14. The bearing assembly according to any one of aspects 1 to 4, characterized in that the adjusting device comprises a piezo element, which is connected to the bearing element in such a way, in particular detachably connected in such a way, that an application of a predetermined voltage to the piezo element causes a displacement of the bearing element by the predetermined distance.

15. A rotary fluid pump for conveying a fluid, in particular a rotary blood pump for conveying blood, comprising a bearing assembly according to any one of the preceding aspects.

The invention claimed is:

1. A bearing assembly for mounting a rotor within a pump housing of a rotary blood pump, the rotor being rotatable about a rotation axis, the bearing assembly comprising:
 a base body;
 a bearing element, which is displaceable relative to the base body in the direction of the rotation axis, for accommodating the rotor; and
 an adjusting device, which is connected to the bearing element, for displacing the bearing element in the direction of the rotation axis by a predetermined distance, the predetermined distance being ≤500 µm, wherein the adjusting device is configured to be situated so as to be operable from outside of the pump housing after installation of the bearing assembly.

2. The bearing assembly of claim 1, wherein the predetermined distance is ≤100 µm.

3. The bearing assembly of claim 1, wherein the adjusting device comprises a fine threaded spindle and a threaded washer, the threaded washer being rigidly connected to the base body, and the fine threaded spindle being rigidly connected to the bearing element in the direction of the rotation axis and screwed into the threaded washer so that a screwing motion of the fine threaded spindle in the threaded washer by a predetermined angle causes a displacement of the bearing element by the predetermined distance.

4. The bearing assembly of claim 3, wherein a spring element is arranged between the bearing element and the threaded washer, which prestresses the fine threaded spindle with respect to the threaded washer.

5. The bearing assembly of claim 3, wherein the adjusting device comprises a lock nut, which can be screwed or is screwed onto the fine threaded spindle on a side of the threaded washer facing away from the bearing element, for fixing a position of the bearing element.

6. The bearing assembly of claim 1, wherein the adjusting device comprises a segment plate including at least four segments arranged in a cross-shaped manner, the segment plate, in two opposing segments, including regions that are raised toward the base body and have a predetermined height, and the base body including recessed regions located opposite the raised regions of the segment plate so that, in a first position of the segment plate, the raised and recessed regions engage one another, and so that a rotation of the segment plate into a second position, in which the raised and recessed regions do not engage one another, causes a displacement of the bearing element by the predetermined distance, the predetermined distance corresponding to the predetermined height of the raised regions.

7. The bearing assembly of claim 6, wherein the adjusting device comprises a fine threaded spindle and a lock nut, and the fine threaded spindle is rigidly connected to the bearing element in the direction of the rotation axis and, on a side facing away from the bearing element, is screwed into the segment plate and fixed in the segment plate by way of the lock nut.

8. The bearing assembly of claim 6, wherein the segment plate comprises a clamping device, the bearing element being inserted into the segment plate in the direction of the rotation axis and being fixed by way of the clamping device.

9. The bearing of claim 6, wherein the raised regions are manufactured by way of a machining process.

10. The bearing assembly of claim 1, wherein the adjusting device comprises a tapered washer including two tapered surfaces that are arranged diametrically offset and inclined in a circumferential direction of the tapered washer, the bearing element being screwed into the tapered washer so that a rotation of the tapered washer by a predetermined angle causes a displacement of the bearing element by the predetermined distance.

11. The bearing assembly of claim 1, wherein the bearing element, on a side of the bearing element facing away from the rotor to be accommodated, includes a wedge-shaped section, and the adjusting device comprises a disk-shaped element having a funnel-shaped through-opening, the bearing element being inserted with the wedge-shaped section into the funnel-shaped through-opening and rigidly connected to a termination element, and the adjusting device further comprising a spring element, which is arranged between the disk-shaped element and the termination element and prestresses the disk-shaped element with respect to the bearing element, and a clamping screw arranged in the disk-shaped element, such that a diameter of the wedge-shaped through-opening is changed by a predetermined amount so that a change of the diameter by a predetermined diameter difference causes a displacement of the bearing element by the predetermined distance.

12. The bearing assembly of claim 1, wherein the adjusting device comprises a lever, which is connected to the bearing element so that a change in an inclination of the lever relative to the base body by a predetermined angular difference causes a displacement of the bearing element by the predetermined distance.

13. The bearing assembly of claim 1, wherein the adjusting device comprises an element having a predetermined coefficient of thermal expansion, wherein the element is connected to the bearing element such that a change of a temperature of the element by a predetermined temperature amount causes a displacement of the bearing element by the predetermined distance.

14. The bearing assembly of claim 1, wherein the adjusting device comprises a piezo element, which is detachably connected to the bearing element in such that an application of a predetermined voltage to the piezo element causes a displacement of the bearing element by the predetermined distance.

15. The bearing assembly of claim 1, wherein the adjusting device comprises a screw element, which is connected to the bearing element such that a rotation of the screw element by a predetermined angle causes a displacement of the bearing element by the predetermined distance.

16. The bearing assembly of claim 15, wherein a rotation of the screw element by 45° causes a displacement of the bearing element by 25 µm.

17. The bearing assembly of claim 1, wherein the adjusting device comprises a screw element connected to the bearing element such that a rotation of the screw element by a predetermined angle causes a displacement of the bearing element by the predetermined distance.

18. The bearing assembly of claim 8, wherein the machining process to manufacture the raised regions is a grinding process and/or an additive process, the additive process including a vapor deposition process, a printing process and/or a coating process.

19. The bearing assembly of claim 1, wherein the adjusting device comprises a clamping element for fixing the bearing element relative to the base body in a direction of the rotation axis.

20. A rotary fluid pump for conveying blood, comprising:

a pump housing;

a bearing assembly for mounting a rotor rotatable about a rotation axis within the pump housing;

a base body;

a bearing element, the bearing element being displaceable relative to the base body in the direction of the rotation axis, including the rotor; and an adjusting device, the adjusting device connected to the bearing element for displacing the bearing element in the direction of the rotation axis by a predetermined distance ≤500 µm, wherein the adjusting device is situated so as to be operable from outside of the pump housing after installation of the bearing assembly.

* * * * *